(12) United States Patent
Stephenson et al.

(10) Patent No.: US 11,353,863 B2
(45) Date of Patent: Jun. 7, 2022

(54) TRAJECTORY BASED MAINTENANCE

(71) Applicant: HALLIBURTON ENERGY SERVICES, INC., Houston, TX (US)

(72) Inventors: Stanley V. Stephenson, Duncan, OK (US); Thomas M. Logan, Norman, OK (US); Sumit Bhat, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 463 days.

(21) Appl. No.: 16/340,100

(22) PCT Filed: Feb. 25, 2019

(86) PCT No.: PCT/US2019/019388
§ 371 (c)(1),
(2) Date: Apr. 5, 2019

(87) PCT Pub. No.: WO2020/176069
PCT Pub. Date: Sep. 3, 2020

(65) Prior Publication Data
US 2021/0325865 A1    Oct. 21, 2021

(51) Int. Cl.
*G05B 23/02* (2006.01)
*G06Q 10/00* (2012.01)
*G06Q 50/02* (2012.01)

(52) U.S. Cl.
CPC ......... *G05B 23/0283* (2013.01); *G06Q 10/20* (2013.01); *G06Q 50/02* (2013.01)

(58) Field of Classification Search
CPC ..... G06Q 50/02; G06Q 10/20; G05B 23/0283

USPC .......................................................... 702/184
See application file for complete search history.

(56) References Cited

U.S. PATENT DOCUMENTS

| | | | |
|---|---|---|---|
| 6,691,064 B2 * | 2/2004 | Vroman | B61L 27/0094 702/113 |
| 6,871,160 B2 | 3/2005 | Jaw | |
| 7,260,501 B2 | 8/2007 | Pattipatti et al. | |
| 9,014,918 B2 | 4/2015 | Hagen et al. | |
| 2002/0148646 A1 | 10/2002 | Schultz et al. | |

(Continued)

FOREIGN PATENT DOCUMENTS

JP        2017102554 A    6/2017

OTHER PUBLICATIONS

International Search Report and Written Opinion for PCT application No. PCT/US2019/019388 dated Nov. 22, 2019, 10 pages.

(Continued)

*Primary Examiner* — John H Le
(74) *Attorney, Agent, or Firm* — Conley Rose, P.C.; Rodney B. Carroll

(57) ABSTRACT

A method includes monitoring work done by a piece of equipment to generate backward-looking usage data. The method includes making a prediction of future work to be done by the piece of equipment, generating forward-looking usage data based on the prediction of future work, and making a prediction of when the piece of equipment is expected to fail based on the backward-looking usage data and on the forward-looking usage data. The method includes operating the piece of equipment after performing the prediction, and removing the piece of equipment from service prior to when the piece of equipment is expected to fail based on the prediction.

18 Claims, 3 Drawing Sheets

(56) References Cited

U.S. PATENT DOCUMENTS

| | | | |
|---|---|---|---|
| 2002/0183971 A1 | 12/2002 | Wegerich et al. | |
| 2004/0254764 A1* | 12/2004 | Wetzer | G06Q 10/0635 |
| | | | 702/184 |
| 2008/0133178 A1* | 6/2008 | Byrne | G05B 23/0283 |
| | | | 702/184 |
| 2012/0283963 A1 | 11/2012 | Mitchell et al. | |
| 2016/0173324 A1 | 6/2016 | Bonawitz et al. | |
| 2017/0206510 A1* | 7/2017 | Horton | G06Q 10/20 |
| 2018/0005461 A1* | 1/2018 | Steketee | E02F 9/2025 |

OTHER PUBLICATIONS

Espen A. Ulimoen, "Condition Monitoring and Condition Based Maintenance" ABB Oil Gas and Chemicals Norway, Apr. 2016, Automation Scandinavia 2016, 17 pages.

Stan Stephenson, "Reliability Centered Maintenance: The Swiss Army Knife of Maintenance", Present at 2015 Applied Reliability Conference, Tucson, AZ, 10 pages.

\* cited by examiner

TRAJECTORY BASED MAINTENANCE

BACKGROUND OF THE INVENTION

1. Field of the Invention

The present disclosure relates to health monitoring for equipment, and more particularly to predicting useful life of equipment before maintenance, replacement, or the like, is required.

2. Description of Related Art

Equipment with mechanical and/or electrical components, such as gas and oilfield equipment, has a finite useable life. At some point, wear and usage bring equipment to a point of failure. It is advantageous to replace equipment prior to failure, but for cost effectiveness, operators desire to operate equipment as long as feasible before failure. Health monitoring traditionally involves gathering data on how a given piece of equipment is used. For example, a health monitoring system can use sensors to record mechanical or electrical loads placed on the equipment. This data can be used, for example in a computer model of the equipment, to predict how much useable life the piece of equipment has before failure. Operators can use this prediction to replace the piece of equipment prior to failure. The more accurate and trustworthy the prediction is, the closer to failure point the operator can keep the piece of equipment in service.

The conventional techniques have been considered satisfactory for their intended purpose. However, there is an ever present need for improved health monitoring and maintenance. This disclosure provides a solution for this need.

BRIEF DESCRIPTION OF THE DRAWINGS

So that those skilled in the art to which the subject disclosure appertains will readily understand how to make and use the devices and methods of the subject disclosure without undue experimentation, preferred embodiments thereof will be described in detail herein below with reference to certain figures, wherein.

DETAILED DESCRIPTION OF THE PREFERRED EMBODIMENTS

Figure 1:
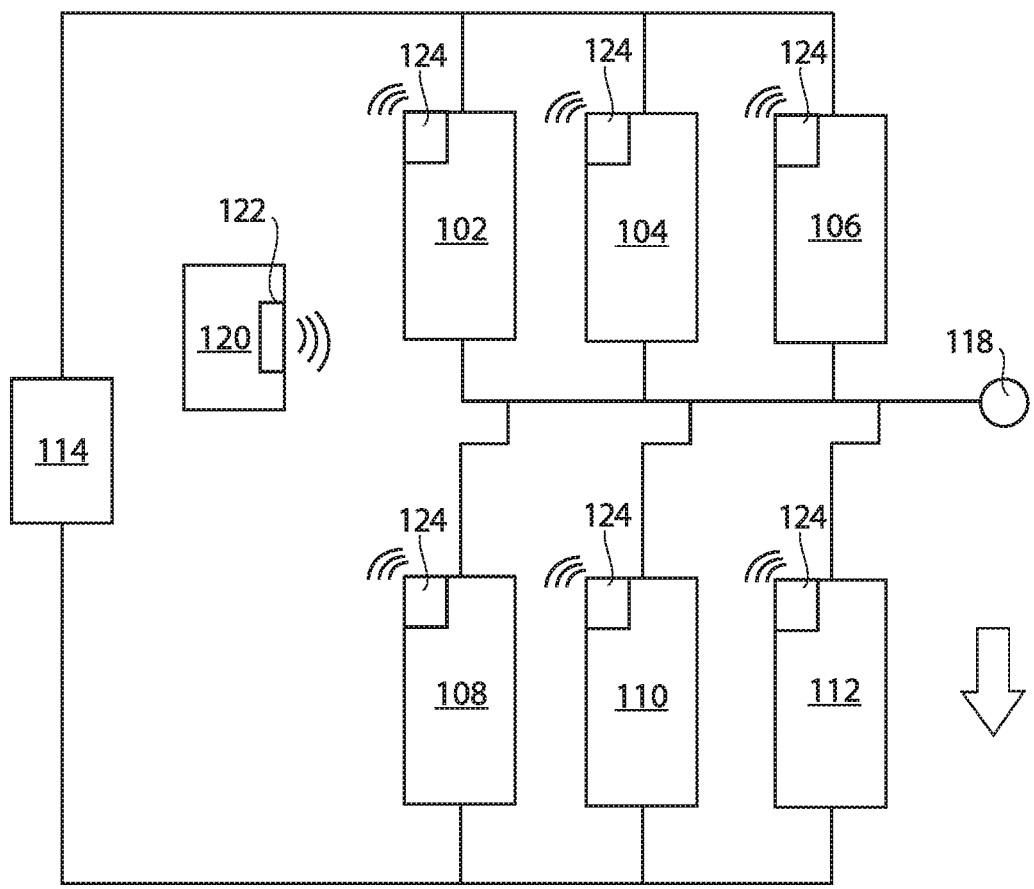
FIG. 1 is a schematic view of an exemplary embodiment of a system constructed in accordance with the present disclosure, showing a control device and a plurality of pieces of equipment monitored by the control device.

Reference will now be made to the drawings wherein like reference numerals identify similar structural features or aspects of the subject disclosure. For purposes of explanation and illustration, and not limitation, a partial view of an exemplary embodiment of a system in accordance with the disclosure is shown in FIG. 1 and is designated generally by reference character 100. Other embodiments of systems in accordance with the disclosure, or aspects thereof, are provided in FIGS. 2-3, as will be described. The systems and methods described herein can be used for equipment monitoring and operation to increased utilization of equipment before failure, maintenance, replacement, or the like, relative to traditional techniques.

The system includes a plurality of pieces of equipment 102, 104, 106, 108, 110, 112. The pieces of equipment can be oilfield equipment, and in this exemplary context, the pieces of equipment 102, 104, 106, 108, 110, 112 are fracture stimulation pumps. Each of the pieces of equipment 102, 104, 106, 108, 110, 112 is connected in fluid communication to a fracturing fluid blender 114 and to a well 118, e.g., for gas and/or oil production. During fracture stimulation, the fracture stimulation pumps can pump a fracture stimulation fluid such as a liquid and sand mixture, slurry, into the well 118. Those skilled in the art having the benefit of this disclosure will readily appreciate that any number of pieces of equipment can be used, and that any suitable type of equipment (e.g., factory machines, vehicles, electrical infrastructure or components, or the like) can be used without departing from the scope of this disclosure.

The system 100 also includes a control device 120 with an input interface 122. The control device 120 includes machine-readable instructions configured to monitor work done by the pieces of equipment 102, 104, 106, 108, 110, 112 to generate backward-looking usage data, and make a prediction of future work to be done by the piece of equipment. Monitoring work done by a piece of equipment can include receiving input from one or more physical state sensors 124 operatively connected to the respective piece of equipment 102, 104, 106, 108, 110, 112. As depicted schematically in FIG. 1, the connection between the physical state sensors 124 and the control device 120 can by wireless, e.g., by wirelessly connecting each of the sensors 124 to the input interface 122 of the control device 122. Those skilled in the art having the benefit of this disclosure will readily appreciate that wired connections can be used in addition to or in lieu of wireless connections. The sensors 124 can be any suitable type of sensor for detecting stress, strain, duty cycles, pressure, temperature, or any other suitable physical parameter for monitoring the health of the respective piece of equipment 102, 104, 106, 108, 110, 112. It is also contemplated that in addition to or in lieu of collecting usage data from physical state sensors 124, monitoring work done by a given piece of equipment 102, 104, 106, 108, 110, 112 can include receiving input indicative of job-type and duration, e.g., user input entered at the input interface 122 wirelessly from another device, or using input devices such as a mouse and/or keyboard or touch screen connected to the input interface 122. For example, the user can enter the number of duty cycles, hours of operation, volume, or the like, indicative of what the piece of equipment 102, 104, 106, 108, 110, 112 has been doing or will be doing in the future.

Figure 2:
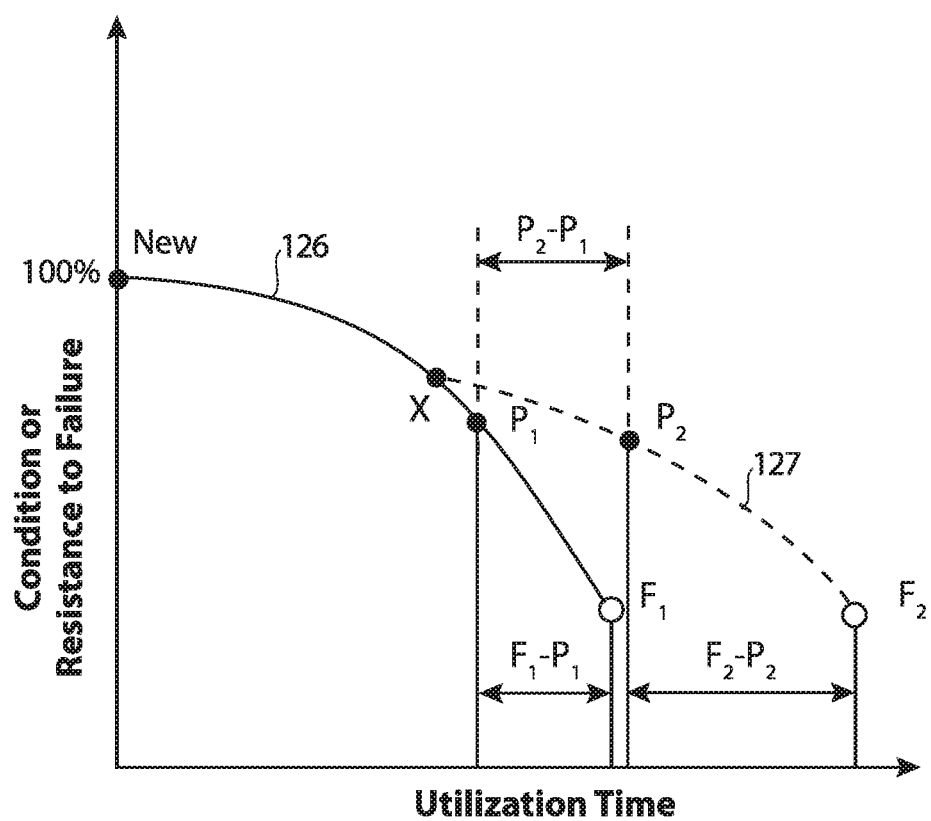
FIG. 2 is a graph schematically indicating performance of one of the pieces of equipment of the system of FIG. 1, showing predicted failures for the piece of equipment using only backward-looking usage data, and using forward- and backward-looking usage data.

With reference to FIG. 2, the control device 120 can model the performance of the piece of equipment 102, 104, 106, 108, 110, 112 using a physical model, and/or statistical model, and/or an empirical, and/or other applicable models based on the backward-looking usage data. The solid curve 126 in FIG. 2 indicates the model's prediction of potential failure P1 in terms of condition as a function of time, and actual failure F1 if the piece of equipment continues to operate as in the back-ward looking usage data. At a point in time X before the potential failure P1, the piece of equipment 102, 104, 106, 108, 110, 112 would have to be removed from service in order to assure actual failure is avoided.

With continued reference to FIG. 2, the control device 120 can generate forward-looking usage data based on the prediction of future work. Using the same model as before, the control device 120 can make a prediction of when the piece of equipment 102, 104, 106, 108, 110, 112 is expected to fail based on the backward-looking usage data and based on the forward-looking usage data. The potential failure P2 using both the backward-looking and the forward-looking usage data may be further along the time line (horizontal axis) in FIG. 2 than the original potential failure P1 using only the backward-looking usage data, especially if the duty load on the piece of equipment 102, 104, 106, 108, 110, 112 is reduced over time. The actual failure F2 can be predicted using the forward-looking usage data together with the backward-looking usage data, and the actual failure F2 can be pushed out beyond the original actual F1. Thus, with a reduction in load on the piece of equipment 102, 104, 106, 108, 110, 112, it can be operated after the control device 120 performs the prediction, and need not be removed from service until just prior to when the piece of equipment 102, 104, 106, 108, 110, 112 is expected to fail based on the prediction of potential failure P2, potentially extending the useable life of the piece of equipment 102, 104, 106, 108, 110, 112 by an amount equal to P2 minus P1. The difference F1 minus P1 can also be increased to F2–P2, increasing the safety margin between potential failure and actual failure.

The prediction can be a first prediction of P1 and F1 can be for the forward-looking data is forward-looking data based on a first job. Generating forward-looking data can be based on a second job that is lighter-duty for the piece of equipment 102, 104, 106, 108, 110, 112 than the first job. A second prediction, e.g., of P2 and F2 on line 127 in FIG. 2, of when the piece of equipment 102, 104, 106, 108, 110, 112 is expected to fail based on the backward-looking usage data and on the forward looking data based on the second job. As shown in FIG. 1, the first job can be on a first location 128 and the second job can be on the same location 128, wherein the second job is the same type of job as the first job but at a reduced duty, as indicated schematically by the downward pointing arrow in FIG. 1. For instance, if the piece of equipment 112 is nearing its potential failure P1 based on back-ward looking usage data derived from its sensor 124, the control device 120 can predict a new potential failure P2 based on reduced loading or volume, e.g., pumping at a lower rate, for the piece of equipment 112. If the new prediction of P2 is significantly further in the future than the original potential failure P1, the control device 120 can cause the piece of equipment 112 to operate at a reduced loading or volume, e.g., pump at a lower rate, on the same location 128. Another way to reduce duty would be to switch the specific type of job, for example to switch the piece of equipment 112 from pumping proppant mixed with water to pumping pure water. This concept can be used, e.g., in a factory setting, where a piece of production equipment is not moved, but is operated on an easier product line, pace, loading, or specific job type to extend its useful life.

Figure 3:
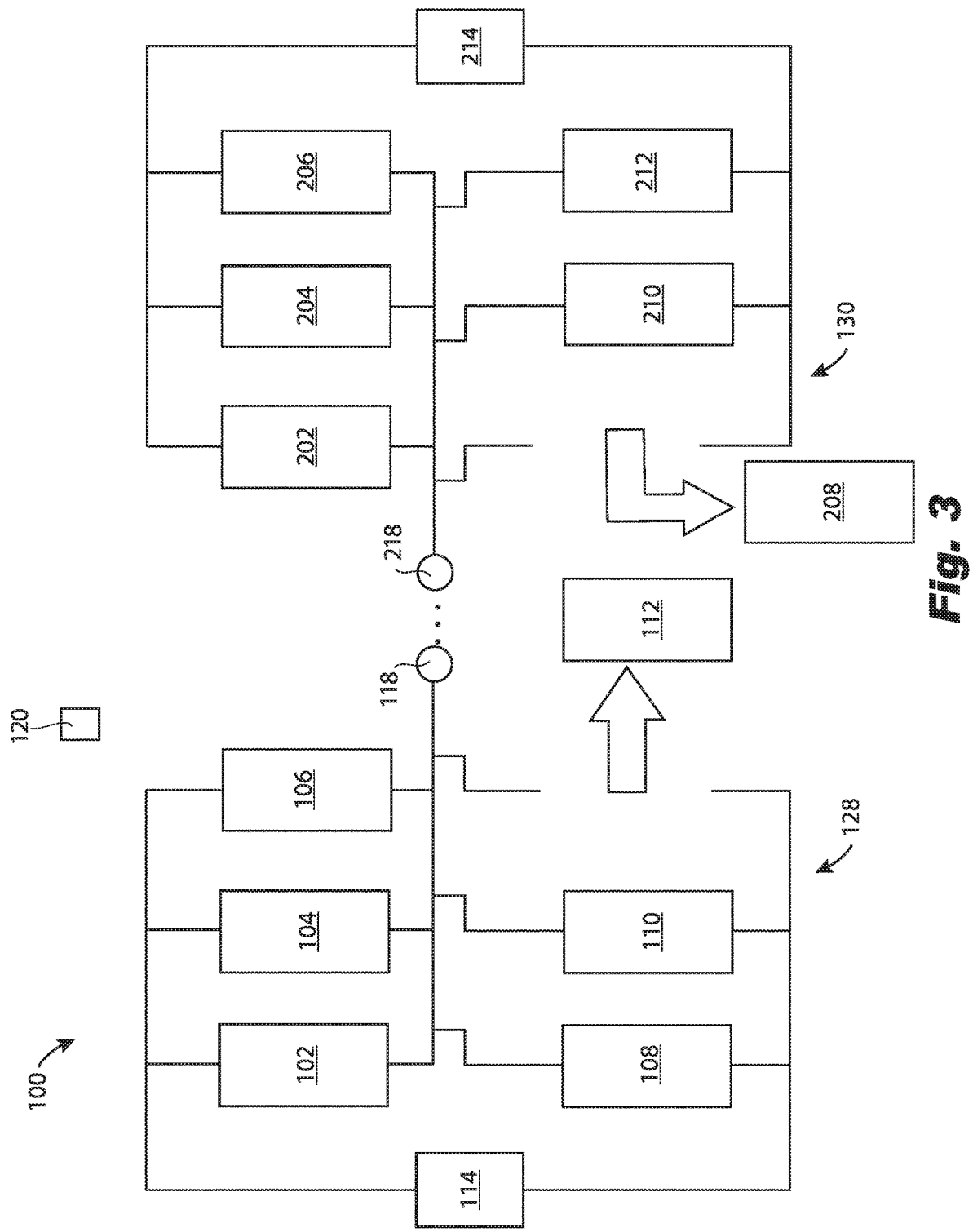
FIG. 3 is a schematic view of the system of FIG. 1, showing movement of one of the pieces of equipment from a first location to a second location to lower the duty on the piece of equipment.

With reference now to FIG. 3, it is also contemplated that the first job can be on a first location 128, and the second job (e.g. with pieces of equipment 202, 204, 206, 208, 210, 212 configured to service well 218 from blender 214 much as described above with respect to FIGS. 1-2) is on a second location 130 different from the first location 128. The piece of equipment 112 can be moved from the first location 128 to the second location 130 after removing the piece of equipment 112 from service on the first job. For example, as schematically indicated by the large arrows in FIG. 3, if the control device 120 predicts longer useful life for the piece of equipment 112 at the second location 130 than in the first location 128, the piece of equipment 112 can be moved before its potential failure P1 to the second location 130 to replace a piece of equipment 208 that is near its own potential failure P1. After the move, the piece of equipment 112 can be operated at the second location beyond the useful life it would have had on the first job in the first location 128. The piece of equipment 112 can be operated on the second job until it needs to be removed from service, e.g., just prior to its new potential failure P2, when it can be removed for maintenance or disposal. Removing the piece of equipment 112 from service on the first job can be performed before reaching a potential failure P1 due to the first job being complete. e.g., if the first job is complete before the potential failure P1, the control device 120 can take that opportunity to evaluate a future job to suit the piece of equipment and further utilize or even maximize the useable life. In another aspect, the control device 120 can specifically select the second job in order to more fully utilize useful life of the piece of equipment 102, 104, 106, 108, 110, 112.

It is contemplated that the control device 120 can be a computer, a plurality of computers, e.g., networked computers, with memory, processor(s), and architecture for performing on machine readable instructions to perform techniques as disclosed herein. The control device 120 can be operatively connected to monitor, operate, and remove the pieces of equipment 102, 104, 106, 108, 110, 112 on an individual basis. For example, the control device 120 can itself control pumping speed or volume to increase useful life of a pump, or more generally to increase duty of the piece of equipment 102, 104, 106, 108, 110, 112, and/or reduce duty of the piece of equipment 102, 104, 106, 108, 110, 112. It is also contemplated that the control device 120 need not necessarily have direct control over the pieces of equipment 102, 104, 106, 108, 110, 112, but can provide output to a separate controller or user who can effect the control of the pieces of equipment 102, 104, 106, 108, 110, 112.

Systems and methods as disclosed herein can allow greater utilization of equipment capital than traditional techniques. It is possible to optimize the useful life of equipment using the systems and methods disclosed herein to maximally utilize the useful life of equipment. This also benefits by reducing downtime on operations using the equipment, and reduces the amount of resources needed for equipment maintenance, replacement, and the like.

Accordingly, as set forth above, embodiments disclosed herein may be implemented in a number of ways. For example, in general, in one aspect, the disclosed embodiments relate to a method of equipment maintenance. The method includes monitoring work done by a piece of equipment to generate backward-looking usage data. The method includes making a prediction of future work to be done by the piece of equipment, generating forward-looking usage data based on the prediction of future work, and making a prediction of when the piece of equipment is expected to fail based on the backward-looking usage data and on the forward-looking usage data. The method includes operating the piece of equipment after performing the prediction, and removing the piece of equipment from service prior to when the piece of equipment is expected to fail based on the prediction.

In general, in another aspect, the disclosed embodiments relate to a system. The system includes a piece of equipment and a control device with an input interface. The control device includes machine-readable instructions configured to monitor work done by the piece of equipment to generate backward-looking usage data, make a prediction of future work to be done by the piece of equipment, generate forward-looking usage data based on the prediction of future work, make a prediction of when the piece of equipment is expected to fail based on the backward-looking usage data and on the forward-looking usage data, operate the piece of equipment after performing the prediction, and remove the piece of equipment from service prior to when the piece of equipment is expected to fail based on the prediction.

In accordance with any of the foregoing embodiments, making a prediction of when the piece of equipment is expected to fail can include predicting potential failure and actual failure, and removing the piece of equipment from service can include removing the piece of equipment from service prior to potential failure. Making the prediction can include using a model of the piece of equipment, and removing the piece of equipment from service can be performed between the potential failure of the piece of equipment as expected based solely on using the backward-looking usage data in the model, and the potential failure of the piece of equipment as expected based on using both the backward-looking usage data and the forward-looking usage data in the model. The model can include at least one of physics based modeling and/or empirical based modeling.

In accordance with any of the foregoing embodiments, the piece of equipment can be a piece of oilfield equipment.

In accordance with any of the foregoing embodiments, monitoring work done by a piece of equipment can include receiving input from one or more physical state sensors operatively connected to the piece of equipment.

In accordance with any of the foregoing embodiments, monitoring work done by a piece of equipment can include receiving input indicative of job-type and duration.

In accordance with any of the foregoing embodiments, the prediction can be a first prediction, wherein the forward-looking data is forward-looking data based on a first job and further comprising: generating forward-looking data based on a second job that is lighter-duty for the piece of equipment than the first job, and making a second prediction of when the piece of equipment is expected to fail based on the backward-looking usage data and on the forward looking data based on the second job. The first job can be on a location, wherein the second job is on the location, wherein the second job is the same as the first job but at a reduced duty. The first job can be on a first location, wherein the second job is on a second location different from the first location, and further comprising: moving the piece of equipment from the first location to the second location after removing the piece of equipment from service on the first job; and operating the piece of equipment on the second job after moving the piece of equipment.

In another aspect, removing the piece of equipment from service can include removing the piece of equipment from service on the first job and further comprising: operating the piece of equipment on the second job, and removing the piece of equipment from service on the second job prior to when the piece of equipment is expected to fail based on the second prediction. Making the prediction of when the piece of equipment is expected to fail can include predicting potential failure and actual failure, wherein removing the piece of equipment from service on the first job includes removing the piece of equipment from service prior to potential failure on the first job. Removing the piece of equipment from service on the first job can be performed before reaching a potential failure due to the first job being complete. The second job can be selected in order to more fully utilize useful life of the piece of equipment.

In accordance with any of the foregoing embodiments, at least one physical state sensor can be operatively connected to the piece of equipment for physical monitoring. The at least one physical state sensor can be operatively connected to the input port of the control device to input data indicative of physical state of the piece of equipment.

In accordance with any of the foregoing embodiments, a user input interface can be operatively connected to the input interface of the control device for input indicative of job-type and duration for the piece of equipment.

In accordance with any of the foregoing embodiments, the control device can be operatively connected to the piece of equipment to increase duty of the piece of equipment and/or reduce duty of the piece of equipment.

In accordance with any of the foregoing embodiments, the piece of equipment can be a first piece of equipment, and further comprising: a plurality of additional pieces of equipment, wherein the control device is operatively connected to monitor, operate, and remove the pieces of equipment on an individual basis.

The methods and systems of the present disclosure, as described above and shown in the drawings, provide for equipment monitoring and operation with superior properties including increased utilization of equipment before failure, maintenance, replacement, or the like. While the apparatus and methods of the subject disclosure have been shown and described with reference to preferred embodiments, those skilled in the art will readily appreciate that changes and/or modifications may be made thereto without departing from the scope of the subject disclosure.

What is claimed is:

1. A method of equipment maintenance comprising:
    monitoring work done by a piece of equipment to generate backward-looking usage data;
    making a prediction of future work to be done by the piece of equipment;
    generating forward-looking usage data based on the prediction of future work;
    making a prediction of when the piece of equipment is expected to fail based on the backward-looking usage data and on the forward-looking usage data;
    operating the piece of equipment after performing the prediction;
    removing the piece of equipment from service prior to when the piece of equipment is expected to fail based on the prediction, wherein the prediction is a first prediction, wherein the forward-looking data is forward-looking data based on a first job;
    generating forward-looking data based on a second job that is lighter-duty for the piece of equipment than the first job, where the second job is the same as the first job but at a reduced duty;
    making a second prediction of when the piece of equipment is expected to fail based on the backward-looking usage data and on the forward-looking data based on the second job, wherein removing the piece of equipment from service includes removing the piece of equipment from service on the first job;
    operating the piece of equipment on the second job; and
    removing the piece of equipment from service on the second job prior to when the piece of equipment is expected to fail based on the second prediction and after the piece of equipment is expected to fail based on the first prediction.

2. The method as recited in claim 1, wherein making a prediction of when the piece of equipment is expected to fail includes predicting potential failure and actual failure, and wherein removing the piece of equipment from service includes removing the piece of equipment from service prior to potential failure.

3. The method as recited in claim 2, wherein making the prediction includes using a model of the piece of equipment, and wherein removing the piece of equipment from service is performed between the potential failure of the piece of equipment as expected based solely on using the backward-looking usage data in the model, and the potential failure of the piece of equipment as expected based on using both the backward-looking usage data and the forward-looking usage data in the model.

4. The method as recited in claim 3, wherein the model includes at least one of physics based modeling and/or empirical based modeling.

5. The method as recited in claim 1, wherein the piece of equipment is a piece of oilfield equipment.

6. The method as recited in claim 1, wherein monitoring work done by a piece of equipment includes receiving input from one or more physical state sensors operatively connected to the piece of equipment.

7. The method as recited in claim 1, wherein monitoring work done by a piece of equipment includes receiving input indicative of job-type and duration.

8. The method as recited in claim 1, wherein the first job is on a location, and wherein the second job is on the location.

9. The method as recited in claim 8, wherein making the prediction of when the piece of equipment is expected to fail includes predicting potential failure and actual failure, and wherein removing the piece of equipment from service on the first job includes removing the piece of equipment from service prior to potential failure on the first job.

10. The method as recited in claim 1, wherein the first job is on a first location, wherein the second job is on a second location different from the first location, and further comprising: moving the piece of equipment from the first location to the second location after removing the piece of equipment from service on the first job; and operating the piece of equipment on the second job after moving the piece of equipment.

11. The method as recited in claim 1, wherein removing the piece of equipment from service on the first job is performed before reaching a potential failure due to the first job being complete.

12. The method as recited in claim 1, further comprising selecting the second job in order to more fully utilize useful life of the piece of equipment.

13. A system comprising:
a piece of equipment;
a control device with an input interface, wherein the control device includes machine-readable instructions configured to:
monitor work done by the piece of equipment to generate backward-looking usage data;
make a prediction of future work to be done by the piece of equipment;
generate forward-looking usage data based on the prediction of future work;
make a prediction of when the piece of equipment is expected to fail based on the backward-looking usage data and on the forward-looking usage data;
operate the piece of equipment after performing the prediction;
remove the piece of equipment from service prior to when the piece of equipment is expected to fail based on the prediction, wherein the prediction is a first prediction, wherein the forward-looking data is forward-looking data based on a first job;
generating forward-looking data based on a second job that is lighter-duty for the piece of equipment than the first job, where the second job is the same as the first job but at a reduced duty;
making a second prediction of when the piece of equipment is expected to fail based on the backward-looking usage data and on the forward-looking data based on the second job, wherein removing the piece of equipment from service includes removing the piece of equipment from service on the first job;
operating the piece of equipment on the second job; and
removing the piece of equipment from service on the second job prior to when the piece of equipment is expected to fail based on the second prediction and after the piece of equipment is expected to fail based on the first prediction.

14. The system as recited in claim 13, wherein the piece of equipment is a piece of oilfield equipment.

15. The system as recited in claim 13, further comprising at least one physical state sensor operatively connected to the piece of equipment for physical monitoring, wherein the at least one physical state sensor is operatively connected to the input port of the control device to input data indicative of physical state of the piece of equipment.

16. The system as recited in claim 13, further comprising a user input interface operatively connected to the input interface of the control device for input indicative of job-type and duration for the piece of equipment.

17. The system as recited in claim 13, wherein the control device is operatively connected to the piece of equipment to increase duty of the piece of equipment and/or reduce duty of the piece of equipment.

18. The system as recited in claim 13, wherein the piece of equipment is a first piece of equipment, and further comprising: a plurality of additional pieces of equipment, wherein the control device is operatively connected to monitor, operate, and remove the pieces of equipment on an individual basis.

* * * * *